United States Patent [19]

Storey

[11] Patent Number: 4,805,630
[45] Date of Patent: Feb. 21, 1989

[54] PRESSURE MONITORING DEVICES

[75] Inventor: Philip A. Storey, Hertfordshire, England

[73] Assignee: The BOC Group, Inc., Montvale, N.J.

[21] Appl. No.: 73,022

[22] Filed: Jul. 14, 1987

[30] Foreign Application Priority Data

Aug. 1, 1986 [GB] United Kingdom ............... 8618845

[51] Int. Cl.$^4$ .............................................. A61B 5/02
[52] U.S. Cl. ..................................... 128/675; 73/705; 250/231 P
[58] Field of Search ............... 128/667, 675; 73/705; 250/231 P

[56] References Cited

U.S. PATENT DOCUMENTS

| 3,215,135 | 11/1965 | Franke | 128/675 |
| 3,580,082 | 5/1971 | Strack | 73/705 |
| 4,210,029 | 7/1980 | Porter | 73/705 |
| 4,547,668 | 10/1985 | Tsikos | 73/705 X |

Primary Examiner—William E. Wayner
Attorney, Agent, or Firm—Larry R. Cassett; Roger M. Rathbun

[57] ABSTRACT

A probe for monitoring the blood pressure of a patient includes a light reflective diaphragm 4 deformable in response to the blood pressure. A single emitter light guide 10 is arranged off-set from the central axis of the diaphragm 4 and directs light at an off-axis region of the diaphragm. A pair of receiver light guides 8, 12 are arranged one on each side of the emitter light guide 10 so that the axes of the light guides lie in or adjacent the same plane as the center of the diaphragm 4. Each receiver light guide 8, 12 receives light reflected from the diaphragm 4 in accordance with movement of the diaphragm 4.

4 Claims, 1 Drawing Sheet

PRESSURE MONITORING DEVICES

BACKGROUND OF THE INVENTION

The present invention relates to pressure monitoring devices and in particular to probes for use in monitoring the blood pressure of a patient.

The measurement of intravascular blood pressure is an important feature of modern health care. In the past intravascular blood pressure has been measured by inserting a catheter into a blood vessel, filling the catheter with a fluid and coupling the catheter by tubing to an external pressure transducer so that the blood pressure is transmitted hydraulically to the pressure transducer.

This type of apparatus has certain disadvantages, for example, when the apparatus is being set up, all traces of air must be meticulously flushed out after slow gravity filling of the apparatus with the hydraulic fluid. During monitoring the apparatus must be periodically checked for the presence of bubbles, which must be removed if found. The infusion of air bubbles into the patient's blood stream can represent a hazard to patient safety as a result of air emboli. Further, air bubbles in the apparatus will effect the accuracy of the apparatus.

Fibre optic pressure sensors offer several advantages over the conventional apparatus referred to above. For example, the small size of fibre optic sensors and their immunity to electromagnetic interference all obtained without recourse to special measures and their attendant costs make fibre optic sensing advantageous particular for in vivo medical applications.

It is known from U.S. Pat. No. 3,215,135 for a blood pressure measuring device to include means in the form of a housing for supporting a light reflecting diaphragm deforamable in response to the pressure of a fluid applied directly to one face of the diaphragm. Two flexible light guides extend into the housing and terminate at a location spaced from and adjacent the diaphragm. In use, one light guide conducts light from a source and emits it on to the opposite face of the diaphragm which reflects a proportional part of the light from the emitter towards a receiver light guide.

In use, when the diaphragm is brought into contact with the fluid the pressure of which is to be determined, the pressure of the fluid will deform the diaphragm and thus alter the intensity of light being received by the receiver light guide. By this means the pressure of the fluid can be determined.

A disadvantage of this known blood pressure measuring device is that there is only one emitter light guide and one receiver light guide positioned symmetrically relative to the reflective face of the diaphragm. This means that should there be any gross or localised reflectively change in the diaphragm this would result in a loss of accuracy. Furthermore, the light guides are in the form of optical fibre bundles which are bulky and relatively rigid.

In a paper entitled "Environmentally Insensitive Diaphragm Reflectance Pressure Transducer" by Christopher M. Lawson and V. J. Tekippe there is disclosed a fibre optic sensor that determines pressure from diaphragm curvature. Light is brought to a reflective surface of the diaphragm by a circle of fibres such that an annular concentric region on the diaphragm is illuminated. Light reflected from the diaphragm is then distributed among receiver fibres arranged concentrically with the emitter fibres both inside and outside of the emitter fibres. The diaphragm deflection is then derived from the ratio of the light received by the outside receiver fibres to that from the inside receiver fibres.

A disadvantage of the fibre optic sensor as described in this paper is that it includes a plurality of emitter fibre optic bundles and a plurality of receiver fibre optic bundles which makes the sensor bulky, relatively rigid and expensive to manufacture.

SUMMARY OF THE INVENTION

It is an aim of the present invention to provide a probe for use in monitoring the pressure of a fluid and more particularly blood in a patient, which is cheap to manufacture but includes all the known advantages of optical fibre sensors.

For the avoidance of doubt the expression "light guide" when used throughout this specification is intended to embrace a single optical fibre, a bundle of optical fibres and a light transmitting rod or rods.

According to the present invention, a probe for use in monitoring the pressure of a fluid comprises a light reflective diaphragm deformable in response to the pressure of said fluid applied directly to one side of the diaphragm, means for supporting the diaphragm for exposing only said one side of the diaphragm to said fluid, a single emitter light guide off-set from the central axis of the diaphragm for directing light at an off-axis region on the opposite side of the diaphragm, a pair of receiver light guides associated with said emitter light guide and arranged one on each side of the emitter light guide so that the axes of the light guides at their distal ends lie in or adjacent the same plane as the centre of the diaphragm, each receiver light guide receiving light reflected from said opposite side of the diaphragm, the proportion of the light that is reflected by the diaphragm and received by each receiver light guide varying in accordance with movement of the diaphragm.

BRIEF DESCRIPTION OF DRAWINGS

Embodiments of the invention will now be described, by way of example, reference being made to the figures of the accompanying diagrammatic drawings in which.

DESCRIPTION OF PREFERRED EMBODIMENT

As shown, a probe 1 for use in monitoring the pressure of a fluid, for example, the blood pressure of a patient includes means in the form of a catheter tube 2 supporting a deformable diaphragm 4. The diaphragm 4 is supported so that one face only is exposed to the fluid whose pressure is being monitored. The diaphragm 4 is light reflective and can be made, for example, of certain plastics or silicon. The diaphragm 4 is deformable in response to the pressure 'P' of the fluid applied directly to its right-hand (as shown) face in FIG. 1.

Figure 1:
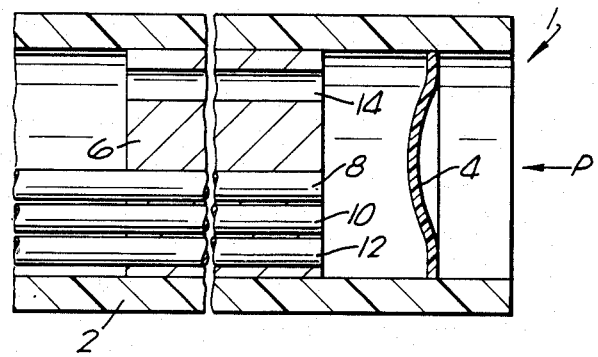
FIG. 1 is a side elevation partly in cross-section of a probe for use in monitoring the pressure of a fluid.
Figure 2:
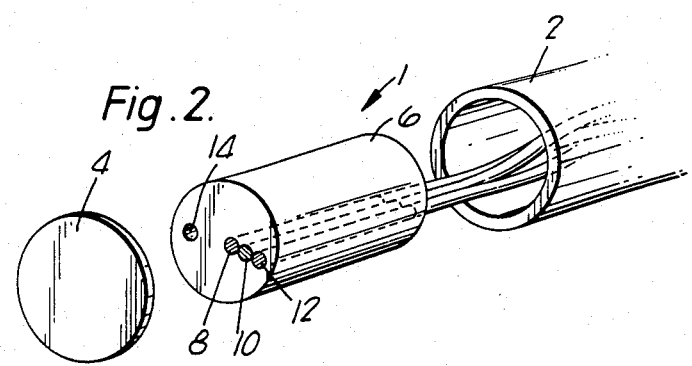
FIG. 2 is an exploded perspective view of the probe of FIG. 1.
Figure 3:
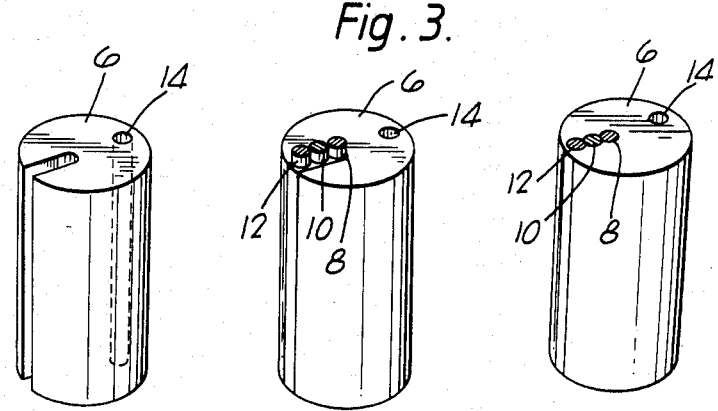
FIG. 3 is a perspective view of a support member and light guides forming part of the probe of FIG. 1.

Immediately to the left (as shown) in FIG. 1 is a support member 6 which is a tight fit within the catheter tube 2. The support member 6 is initially formed with a radial slot extending along the length of the support member which slot accommodates the distal ends of three light guides 8, 10, 12. A passage 14 is also formed longitudinally through the support member 6.

Of the three light guides, all of which in this embodiment of the invention are single optical fibres, the middle light guide 10 is off-set from the central axis of the diaphragm 4 and is used as a light emitter for directing light on to an off-axis portion of the diaphragm 4. The outer and inner light guides 8, 12 are each arranged to receive some of the light reflected from the diaphragm 4.

As is known in the art, at their proximal ends the receiver light guides 8, 12 are each arranged adjacent a light sensor, for example, a photo diode and the emitter light guide 10 is arranged adjacent a source of light, for example a light emitting diode.

In use, the catheter tube 2 is placed in a patient's vein or artery so that blood pressure acting against the right-hand (as shown in FIG. 1) face of the diaphragm causes deflection of the diaphragm. The opposite side of the diaphragm 4 is vented to atmosphere via the passage 14. The angular deflection of the diaphragm 4 is sensed and a measure of pressure derived from the ratio of light received by the receiver light guides 8, 12.

A particular advantage of the embodiment described above is, that since pressure is obtained from a ratio of light intensities then this technique compensates for variations in light source intensity, for loses in the fibres and for variations in the diaphragm reflectance.

It is preferred, that the emitter light guide has a lower numerical aperture than each receiver light guides 8, 12. Modifications can be made to the probe 1, for example, the diaphragm 4 could be arranged at the distal end of the catheter tube 2. Furthermore, an aperture could be formed in the wall of the catheter tube 2 to the left (as shown) in FIG. 1 of the support member 6 giving access from the interior of the tube to the vein or artery of a patient for the infusion of a drug.

The probe 1 can be made as a disposable product in view of its simplicity and hence relative cheapness to manufacture. The catheter tube is small having an outside diameter in the region of 2 millimeters and can be made of flexible material suitable for placement in the vein or artery of a patient.

I claim:

1. A probe for use in monitoring the pressure of blood contained within a blood vessel of a patient comprising a catheter tube having a distal end for placement within the blood vessel, a flexible diaphragm having a central axis and mounted at the distal end of said catheter tube and having one side directly contacting the blood and the other side reflective, said flexible diaphragm being deformable in response to changes in pressure of the blood, a cylindrical support member fitted within said catheter tube and facing said reflective side of said flexible diaphragm, said cylindrical support member having a radial slot formed therein, a single emitter light guide fitted within said slot and offset from the central axis of said flexible diaphragm for directing light at an off axis region of said reflective side of said flexible diaphragm, a pair of receiver light guides fitted within said slot and radially aligned on either side of said emitter light guide, said receiver light guides receiving light reflected from said reflective side of said flexible diaphragm from said light emitter, the proportion of the light that is reflected by said flexible diaphragm and received by each of said receiver light guides varying in accordance with deformation of said diaphragm.

2. A probe as claimed in claim 1, in which the support member is formed with a through passage for venting said opposite side of the diaphragm to atmosphere.

3. A probe as claimed in claim 1, in which the emitter light guide has a lower numerical aperture than each receiver light guide.

4. A probe as claimed in claim 1, in which each light guide in in the form of a single optical fibre.

* * * * *